US011083368B2

(12) United States Patent
Themelis (10) Patent No.: US 11,083,368 B2
(45) Date of Patent: Aug. 10, 2021

(54) SYSTEM AND METHOD, IN PARTICULAR FOR MICROSCOPES AND ENDOSCOPES, FOR CREATING HDR MONOCHROME IMAGES OF A FLUORESCING FLUOROPHORE

(71) Applicant: Leica Instruments (Singapore) Pte. Ltd., Singapore (SG)

(72) Inventor: George Themelis, Lindau (DE)

(73) Assignee: Leica Instruments (Singapore) Pte. Ltd., Singapore (SG)

( * ) Notice: Subject to any disclaimer, the term of this patent is extended or adjusted under 35 U.S.C. 154(b) by 0 days.

(21) Appl. No.: 16/716,589

(22) Filed: Dec. 17, 2019

(65) Prior Publication Data

US 2020/0196846 A1 Jun. 25, 2020

(30) Foreign Application Priority Data

Dec. 20, 2018 (EP) .................................... 18214911

(51) Int. Cl.
*A61B 1/00* (2006.01)
*A61B 1/05* (2006.01)
*G02B 21/36* (2006.01)
*H04N 5/225* (2006.01)

(52) U.S. Cl.
CPC ............ *A61B 1/05* (2013.01); *A61B 1/00004* (2013.01); *A61B 1/00186* (2013.01); *G02B 21/365* (2013.01); *H04N 5/225* (2013.01); *H04N 2005/2255* (2013.01)

(58) Field of Classification Search
CPC ................. G02B 21/365; H04N 5/225; H04N 2005/2255; A61B 1/05; A61B 1/00004; A61B 1/00186
See application file for complete search history.

(56) References Cited

U.S. PATENT DOCUMENTS

| 2009/0173892 A1 | 7/2009 | Courtney et al. |
| 2011/0009163 A1 | 1/2011 | Fletcher et al. |
| 2011/0064296 A1 | 3/2011 | Dixon |
| 2012/0150045 A1 | 6/2012 | Matsumoto et al. |
| 2015/0022647 A1* | 1/2015 | Takei ................. A61B 1/00186 348/70 |

(Continued)

FOREIGN PATENT DOCUMENTS

WO 2014125724 A1 8/2014

*Primary Examiner* — John R Schnurr
(74) *Attorney, Agent, or Firm* — Hodgson Russ LLP (57) ABSTRACT

A method and system for computing an HDR image (38) from a digital color input image (4) of an object (30) containing a fluorescing fluorophore (22) acquires the input image using a color camera (2) having at least two different types (16, 17, 18) of color sensor (8), such as an R, G and B sensor. The input image may be recorded in a co-sensing wavelength band (64, 66, 68) wherein different spectral responsivities (58, 60, 62) of the different types of color sensor overlap. The input image comprises different digital monochrome input images (6), each recorded by a different type of color sensor. Light incident on the camera may be filtered using a band-pass filter (32) having a tunable pass band (34) which defines the co-sensing wavelength band and may be adjusted depending on spectral responsivities of the color sensors, the fluorophore, and characteristics of the monochrome input images.

13 Claims, 4 Drawing Sheets

(56) References Cited

U.S. PATENT DOCUMENTS

2015/0297073 A1   10/2015  Nguyen et al.
2017/0112354 A1*  4/2017  DiCarlo ................... H04N 9/04
2018/0049644 A1    2/2018  Themelis
2018/0373017 A1* 12/2018  Dixon .................. G02B 21/367

* cited by examiner

SYSTEM AND METHOD, IN PARTICULAR FOR MICROSCOPES AND ENDOSCOPES, FOR CREATING HDR MONOCHROME IMAGES OF A FLUORESCING FLUOROPHORE

CROSS REFERENCE TO RELATED APPLICATIONS

This application claims priority of European patent application number 18214911.2 filed Dec. 20, 2018, the entire disclosure of which is incorporated by reference herein.

FIELD OF THE INVENTION

The invention relates to a system and a method for creating High Dynamic Range (HDR) monochrome images of a fluorescing fluorophore.

During surgery or during a pathological examination of a biopsy, fluorophores are used to mark specific types of tissue, cells or parts of a cell. The fluorescence of a fluorophore is triggered by light covering the fluorescence excitation spectrum of the fluorophore. Upon excitation, the fluorophore emits fluorescence in a fluorescence spectrum. Light intensities in the fluorescence spectrum are typically low, resulting in low-contrast fluorescence images even if all other wavelengths not falling within the fluorescence spectrum are blocked.

When within the same image areas of very low and very high intensity coexist, then the dynamic range of the imaging sensor might not be sufficient to capture both high and low intensities. This results in losing the intensity information for the brightest, or/and darkest intensities. In that case all areas with intensity below the lowest level will be presented as black and all intensities above the highest level will be presented as white.

The problem of limited dynamic range does not only occur in cases that high and low intensities are exhibited simultaneously, but also sequentially. In such cases the adjustment of the camera sensitivity could mitigate the problem, but rapid intensity changes might not be able to be compensated fast enough by adjustment of the sensitivity. For example, when fluorescence dye, such as indocyanine green (ICG), is injected intravenously for fluorescence angiography, then the fluorescence signal will be start as very dark, and then upon the arrival of the dye bolus, the signal will become rapidly very high, resulting in a few frames with saturated areas due to the delay of the camera sensitivity auto-adjustment.

Even when the imaging sensor (e.g. CCD, CMOS) has high nominal dynamic range, this often refers to digitization circuit and does not reflect the overall dynamic range of the sensor. For example, even if the output signal is 14 bit, i.e. ~16K different signal levels, the sensor can only distinguish 1000 different light intensity levels. Typically, the dynamic range is increased by capturing multiple images sequentially with a single sensor at different exposure levels so that each subsequent image captures a different dynamic range, e.g. one image for the low intensities, and another for the high intensities. The images are then merged in a way that the dynamic ranges are combined and both the brightest and darkest areas are visualized in a single image. This approach, however, cannot be used for video capture.

The presence of high and low intensity of the fluorescence images results in a low contrast and the loss of valuable information in the process of recording the fluorescence image. To retain this information, it is an object of the system and method according to the invention to create fluorescence images which have an increased dynamic range without the use of expensive additional equipment and which can be used for video.

SUMMARY OF THE INVENTION

To solve this problem, the invention provides an image acquisition system, in particular for a microscope or endoscope, for processing digital input images of a fluorescing fluorophore, and a method for creating a digital monochrome HDR fluorescence image from at least two digital monochrome input images of at least one fluorophore.

According to the invention, the image acquisition system comprises a color camera, the color camera having at least two different types of color sensor, a plurality of input pixels, each type of color sensor generating a different digital monochrome input image comprising the input pixels and having a different spectral responsivity, the color camera further comprising at least one co-sensing wavelength band in which the respective spectral responsivities of at least two sensors at a pixel overlap; and an HDR image generator coupled to the color camera; wherein the HDR image generator is configured to compute a digital monochrome HDR fluorescence output image from the at least two digital monochrome input images.

Further, the method comprises the steps of acquiring at least two digital monochrome input images of the fluorescing fluorophore using at least two different types of color sensor, the at least two different types of color sensor having a different spectral responsivity and comprising at least one co-sensing wavelength band in which the spectral responsivities of the at least two types of sensor overlap, selecting the fluorophore to have a fluorescence spectrum which overlaps with the co-sensing wavelength band; and computing a digital monochrome HDR fluorescence image from the at least two digital monochrome input images.

Thus, the system and method according to the invention are able to provide an HDR image of the fluorescing fluorophore by using e.g. a standard color camera, such as an RGB camera that has three different types of color sensor for each pixel, namely an R (red), a G (green) and a B (blue) color sensor. The HDR images are generated by acquiring a separate monochrome image from each type of color sensor. By using the different responsivities of the different types of color sensor in the co-sensing wavelength band, the different exposure levels necessary for an HDR image are generated automatically.

The above system and method can be further improved by adding one or more of the following additional features, of which each can be added independently of the other, and each is advantageous on its own. The additional features described below may each be applied to both the method and the system.

For example, it is preferred that the digital monochrome images are acquired only in the at least one co-sensing wavelength band. This makes sure that the digital monochrome input images are recorded at different responsivities, i.e. at a different mean intensity level.

Further, it is preferred that the spectral responsivities, in particular the mean spectral responsivities, of at least two, preferably at least three, different types of color sensor differ in the at least one co-sensing wavelength band.

The system may, according to another embodiment, comprise an optical band-pass filter having at least one pass band, the at least one pass band overlapping both the at least one co-sensing wavelength band and the fluorescence wavelength band. Use of such a band-pass filters allows the proper co-sensing wavelength band to be selected, where the respective spectral responsivities of the at least color sensors are sufficiently different to enhance the dynamic range of the resulting HDR image. The optical band-pass filter is preferably located in front of the color camera for filtering light reaching the color camera, or the different types of color sensor, respectively.

Preferably, the pass band of the optical band-pass filter is restricted to a co-sensing wavelength band in which the spectral responsivity of each of the at least two, preferably three, color sensors is different. Most preferably, the spectral responsivities of the at least two or three color sensors have their maximum difference in the pass band of the band-pass filter. The maximum difference may be computed from the mean spectral responsivity of the color sensor in the pass band. The mean spectral responsivity can be computed by using the geometric, arithmetic and/or harmonic mean, and/or the median. The maximum difference may be computed by maximizing the sum of the absolute values of the differences between each of the spectral responsivities in the pass band, and/or by maximizing the product of the differences and/or the mean difference. Only those spectral responsivities that are located above and/or below a corresponding predetermined threshold—e.g. above 40% and/or below 90% of the dynamic range—may be considered in the pass band for computing the maximum difference.

Further, it may be advantageous if the spectral responsivities of the color sensors, in particular their mean values as calculated above, are staggered at least approximately equidistantly in the pass band. The distance between the spectral responsivities may be computed linearly or in a log scale. Variation of +/−20% may still be considered as equidistant.

Each of the above features allows the dynamic range covered by the digital monochrome input images to be maximized.

The pass band may, in one embodiment, be adjusted depending on the fluorescence spectrum of the at least one fluorophore and the spectral responsivities in the co-sensing wavelength band by exchanging the band-pass filter manually.

According to another preferred embodiment of the invention, the pass band may be modified without the need to exchange the band-pass filter. For this, the band-pass filter may be a tunable band-pass filter. The tunable band-pass filter may comprise a tunable pass band which is tunable with respect to at least one of a center frequency of the pass band, at least one cut-off frequency of the pass band, a roll-off at at least one cut-off frequency, and a Q-factor. For example, the tunable optical band-pass filter may be a liquid crystal filter, a fiber-optic filter or a tunable band-pass filter based on interferometry.

The pass band may be adjusted during operation of the image acquisition system, preferably automatically. For such an automatic adjustment of the pass band, the image acquisition system may comprise a filter controller for changing the pass band, preferably depending on an image characteristic of the digital monochrome input images and/or the digital monochrome HDR output image. The image characteristic may comprise at least one of a mean intensity, an intensity histogram, a variance of the intensity and a dynamic range of the fluorescing fluorophore.

According to one embodiment, the pass band may changed automatically based on a feedback loop. As a correcting variable in such a feedback loop, an image characteristic of the at least two monochrome input images and/or the digital monochrome HDR output image may be used. For example, the pass band may be automatically modified to maximize fluorescence intensity in the pass band. The fluorescence intensity in the pass band may be computed by determining an average or mean intensity or brightness of at least one of the at least two digital monochrome input images and/or the digital monochrome HDR output image.

Alternatively or cumulatively, the pass band may be automatically modified, e.g. by the feedback loop, to increase the difference between the mean spectral responsivities in the pass band. Such a difference may be determined by comparing the mean intensity of the at least two digital monochrome input images with one another. Further, alternatively or cumulatively, the pass band may be modified to include the fluorescence wavelength at which the fluorescence intensity is at its maximum level. Such wavelengths may be stored for a variety of different fluorophores.

In another embodiment, the pass band may be changed automatically depending on the fluorophore. For example, the type of fluorophore may be entered manually and the pass band may be adjusted automatically. Such an adjustment may be made using e.g. values for fluorophore-dependent pass bands that have been determined empirically and are stored in the image acquisition apparatus.

In another embodiment, which may be used separately or in addition to the above embodiments, the pass band may be modified for the digital monochrome HDR fluorescence output image to have a mean maximum dynamic range across at least some output pixels of the monochrome input images.

Alternatively or cumulatively, the pass band may be modified to include at least one spectral responsivity located in the middle of a dynamic range of a color sensor. The middle dynamic range is at 50%+/−15% of the overall dynamic range. If e.g. the maximum intensity value at one pixel of an 8-bit color sensor is 255, the middle dynamic range is at an intensity value of 128+/−38.

For performing such an automatic adjustment of the pass band, the filter controller of the image acquisition system may be configured to compute a mean intensity of at least some pixels of at least one monochrome input image, and to modify the pass band depending on that intensity. Alternatively or additionally, the spectral responsivities of the different types of color sensor may be stored in the image acquisition system and used to automatically adjust the pass band. The image acquisition system, in particular the HDR image generator, may be configured to adjust the pass band depending on the spectral responsivities of the different types of color sensor. The image acquisition system, in particular the HDR image generator, may be configured to automatically compute an overlap of the spectral responsivities and to adjust the pass band to at least partly overlap the overlap of the spectral responsivities.

The limiting wavelengths, i.e. the ends, of the co-sensing wavelength band may be specified manually and the automatic adjustment of the pass band may be limited to fall within these limits.

The color camera may be an RGB camera, a CYGM camera or an RGBE camera. The color camera may include a mosaic filter arrangement, such as a Bayer filter, a CYGM filter, an RGB filter and/or it may comprise a Foveon sensor architecture, a color co-site sampling architecture, dichroic mirrors and/or a transparent diffractive filter array. The color camera may also be a multi-spectral or hyper-spectral camera. At least two different types of color sensor are required, preferably at least three. The number of co-sensing bands is preferably one lower than the number of different sensor types. Each type of sensor records a different color band.

The HDR image generator and the filter controller may each be implemented as a hardware device, as a software device, or as a combination of both a hardware and a software device. For example, the HDR image generator and/or the filter controller may comprise at least one CPU, at least one GPU and/or at least one ASIC, and/or a software module which in operation carries out the required function. It is to be noted that, in operation, the software may cause structural changes to the hardware device so that the latter may operate as an HDR image generator and/or a filter controller. These operational changes may e.g. relate to changes of electronic component such as transistors and storage elements.

According to one embodiment, the at least two digital monochrome input images are part of a single frame. The at least two monochrome input images are thus recorded at substantially the same time, so that there is no motion blurring in the resulting HDR output image.

The invention in particular may relate to a medical observation apparatus, such as a microscope or an endoscope, comprising an image acquisition system in one of the above embodiments and/or adapted to carry out the above-described image processing method.

Finally, the invention relates to a non-transitory computer-readable medium storing a program causing a computer to execute the image processing method according to any of the above embodiments.

BRIEF DESCRIPTION OF THE DRAWING VIEWS

In the following, an exemplary embodiment of the invention is described with reference to the drawings. In the drawings, elements that correspond to one another with respect to at least one of function and structure are provided with the same reference numerals.

The combination of features shown and described in the figures is used for explanation only and does not limit the invention to the combination shown and described. In particular, one or more of the above-described optional features may be omitted from the embodiment if the technical effect obtained is not needed for a particular application; and vice versa: one or more additional features described as optional above may be added to the shown embodiment if the technical effect of that one or more features is needed for a particular application.

In the figures.

DETAILED DESCRIPTION OF THE INVENTION

Figure 1:
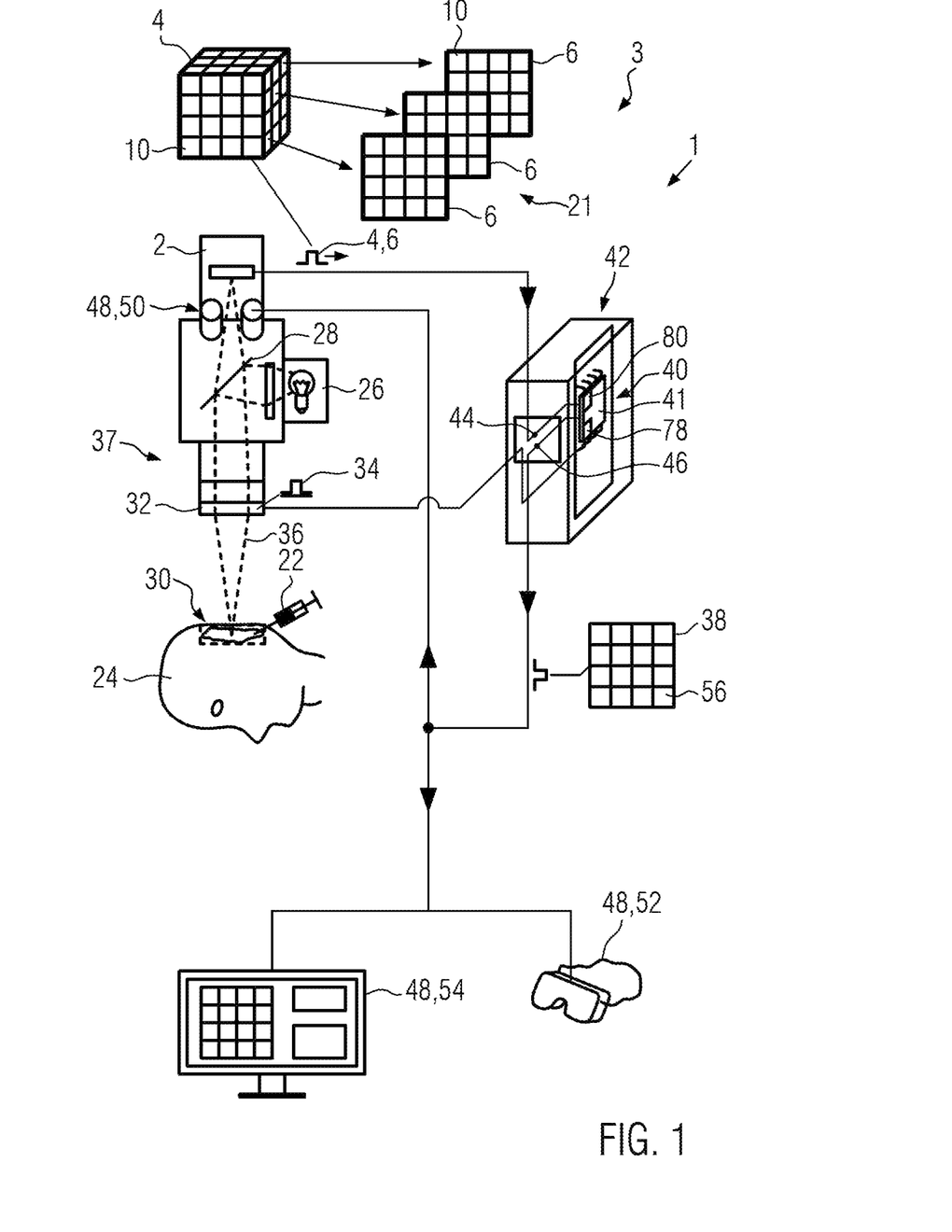
FIG. 1 shows a schematic rendition of an image acquisition system according to the invention.
Figure 2:
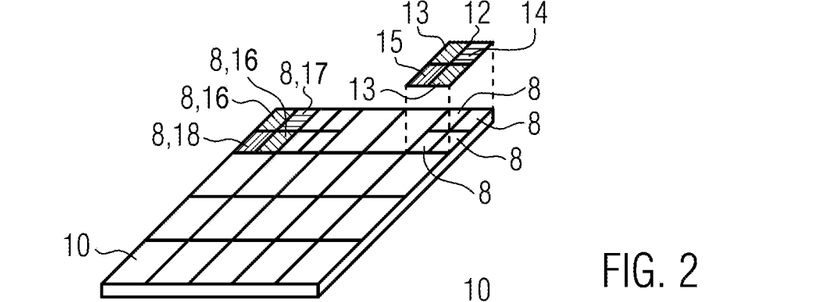
FIG. 2 shows a schematic rendition of a color sensor as used in the image acquisition system of FIG. 1.
Figure 3:
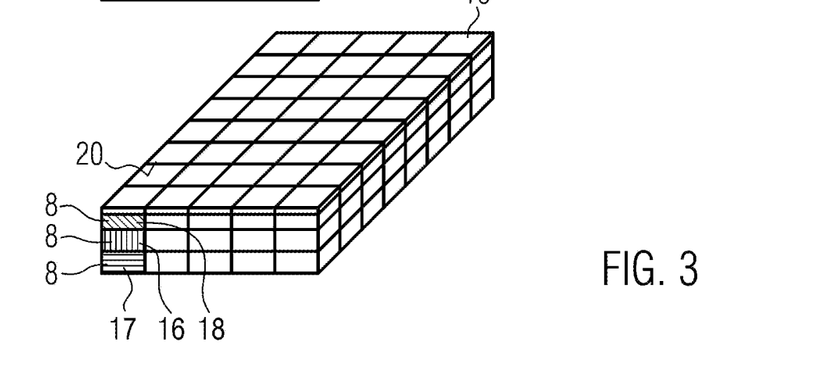
FIG. 3 shows a schematic rendition of another color sensor as used in the image acquisition system of FIG. 1.

An image acquisition system 1 according to the invention may comprise a color camera 2, such as an RGB camera, a multispectral camera or a hyperspectral camera. An RGB camera 2 typically records a digital color input image 4 comprising three different monochrome images 6. Each of the digital monochrome input images 6 has been recorded by a different type of color sensor 8, as shown in FIGS. 2 and 3. Each type of color sensor 8 represents a different color band at an input pixel 10 in the digital color input image 4. Each of the digital input images 4, 6 may be represented by a two- or, generally, n-dimensional array of digital values representing e.g. light intensity.

The different digital monochrome input images 6 may be generated by e.g. providing a mosaic filter arrangement 12 such as a Bayer filter, a CYGM filter or an RGBE filter. Only for exemplary purposes, FIG. 2 shows an RGB filter where, at each pixel 10, two green filters 13, a red filter 14 and a blue filter 15 are used in front of each color sensor 8. The green filter 13 allows only visible green light to pass through it, the red filter 14 only visible red light and the blue filter 15 only visible blue light. Thus, three different types of sensor 16, 17, 18 are provided, with each sensor 16, 17, 18 being sensitive to light in a different color band. The expression "type of color sensor" does not necessarily require a structural difference to exist between the different types 16, 17, 18 of sensor 8, but may require at least a functional difference, namely that each type 16, 17, 18 of color sensor 8 records a different color or wavelength band.

FIG. 3 shows another arrangement of color sensors 8. Here, the color sensed by the different types 16, 17, 18 of color sensor 8 is determined by its depth from a surface 20. As the penetration depth of the visible light depends on the wavelength, blue light penetrates less deeply than green light, and green light penetrates less deeply than red light. Thus, the color sensors 8 are stacked one above the other for each pixel 10.

The invention works for any of these configurations having at least two different types 16, 17, 18 of color sensor 8. However, three or more different types of color sensor are preferred. Preferably, the different digital monochrome input images 6 are part of the same frame 21, i.e. have been taken simultaneously.

The image acquisition system 1 is adapted to record images 4, 6 of a fluorescing fluorophore 22 (FIG. 1), in particular of a fluorophore 22 in live tissue 24 as is the case in surgical microscopes or endoscopes. Alternatively the fluorophore 22 may also be used in a laboratory microscope having a larger magnification, e.g. to visualize parts of a cell, as well as in any other type of microscope or endoscope.

The image acquisition system 1 may comprise a light source 26 which generates light at wavelengths that trigger fluorescence in the fluorophore 22. The light 28 from the light source 26 is directed onto an object 30 containing the fluorophore 22, such as the live tissue 24. The fluorescence emitted from the fluorophore 22 is recorded by the color camera 2 in the at least two digital monochrome input images 6.

The light source 26 may also include white light so that a visible-light image can be recorded at the same time as the image containing the fluorescence light. To acquire a visible-light image, another camera (not shown) may be used which is decoupled by an optical filter arrangement (not shown) from the fluorescence excitation and emission bands, so that these wavelengths are not recorded in the visible-light images.

Figure 4:
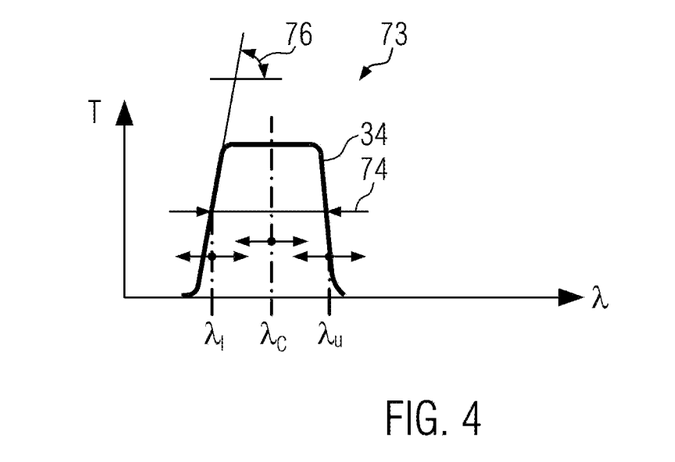
FIG. 4 shows a schematic rendition of a pass band of a band-pass filter of the image acquisition system of FIG. 1.

In this case, the color camera 2 may be solely devoted to recording fluorescence images and may be decoupled from both the excitation wavelengths of the light source 26 and any white light by a band-pass filter 32. The band-pass filter 32 may comprise one of more optical filters which, in combination, result in only wavelengths that fall within a pass band 34 being able to pass through the band-pass filter, as shown schematically in FIGS. 4 and 5, where transmittivity T of the band-pass filter is shown for different wavelengths λ. Alternatively, a multispectral or hyperspectral camera may be used which simultaneously records white-light and fluorescence images in a plurality of, e.g. at least four, wavelength bands using a corresponding number of different types of color sensor. Each digital monochrome input image 6 is recorded by a different type of color sensor.

The band-pass filter 32 is located in front of the camera 2 in an optical path 36 of an optical acquisition system 37 of the image acquisition system 1, which may also comprise the camera 2. If an endoscope is used, the optical path is directed through an optical fiber (not shown) to the object 30.

For computing digital monochrome HDR output images 38, the image acquisition system 1 comprises an HDR image generator 40, which may be a hardware device 41, such as a CPU of a general-purpose computer 42, and/or may comprise a GPU, FPU and/or an ASIC. Alternatively or cumulatively, the HDR image generator 40 may consist of or comprise a software module. The digital color input image 4 or the digital monochrome input image 6, respectively, may be input into the HDR image generator 40 via an input interface 44, which may be configured to accept e.g. RGB, HDMI, DVI or other input formats suitable for transmitting image or video data.

The digital monochrome output image 38 may be output in the same or in a different image format using an output interface 46.

The HDR image generator 40 is adapted to compute the digital monochrome HDR output image 38 from at least two of the digital monochrome input images 6. The digital monochrome HDR output image 38 is displayed on at least one display device 48, such as an eyepiece 50, AR goggles 52 or a monitor 54. As any of the digital color input image, the digital monochrome input image 6 and the digital monochrome HDR output images 38 may be stereoscopic, one or more of the display devices 48 may also be stereoscopic.

The HDR image generator 40 may be adapted to blend the digital monochrome HDR output image 38 with a visible-light image and/or to assign a pseudo-color to the digital monochrome HDR output image 38 depending on the intensity value at an output pixel 56.

It is to be noted that the digital input images 4, 6 and the digital monochrome HDR output image 38 may be part of a time-series of input and output images which result in a video sequence. Each digital monochrome HDR output image 38 is preferably computed and output in real-time by the HDR image generator 40, and displayed in real-time by any of the display devices 48. Moreover, if it is stated in this description that the digital monochrome HDR output image 38 is based on the digital monochrome input images 6, this also includes cases in which two or more monochrome input images 6 of one or more types of color sensor 8 may be averaged to result in a single digital monochrome input image 6 which is then used to compute the digital monochrome HDR output image 38.

Figure 5:
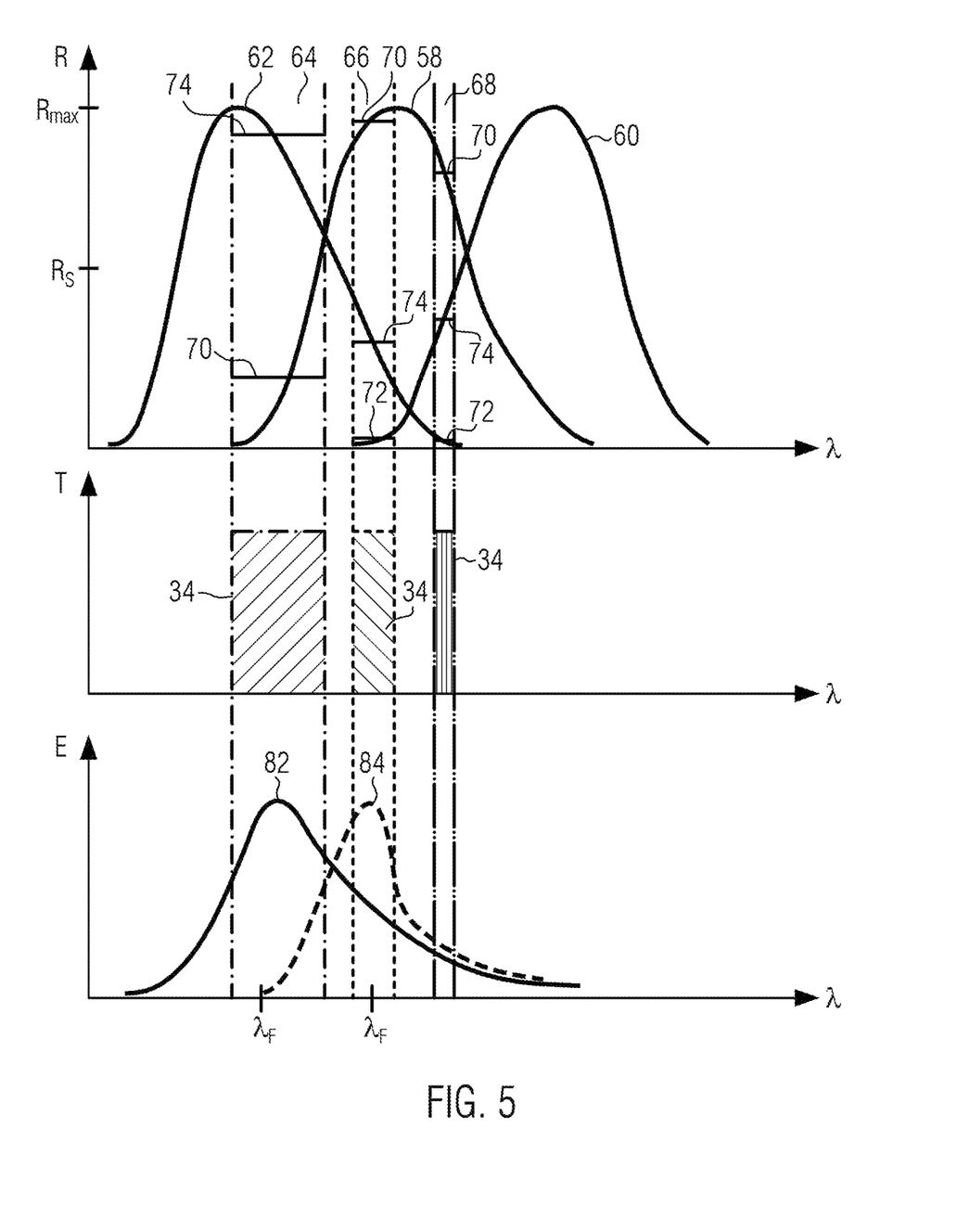
FIG. 5 shows a schematic rendition of spectral responsivities of different types of color sensor, various pass bands of one or more band-pass filters and various fluorescence wavelength bands of fluorophores as used in the image acquisition system of FIG. 1.

The computation of the digital monochrome HDR output image 38 is described in closer detail with reference to FIG. 5.

In the topmost part of FIG. 5, the spectral responsivities R of the different types 16, 17, 18 of color sensor 8 (FIGS. 2 and 3) in the exemplary case of an RGB camera are denoted with reference numerals 58, 60, 62, and shown to be dependent on the wavelength λ. The spectral responsivities R shown have been normalized to a common maximum value $R_{max}$. The curve 60 denotes the spectral responsivity of the color sensor 8 sensing light from the red visible-light spectrum. The curve 58 shows the spectral responsivity of the color sensor 8 sensing light from the green visible-light spectrum. The curve 62 denotes the spectral responsivity of the color sensor 8 sensing light from the blue visible-light spectrum. All spectral responsivities R are shown schematically only and have been normalized.

Also shown in the topmost part of FIG. 5 are examples of co-sensing wavelength bands 64, 66, 68. In a co-sensing wavelength band 64, 66, 68, the spectral responsivities 58, 60, 62 of at least two types 16, 17, 18 of color sensor 8 overlap. For example, in co-sensing wavelength band 64, the spectral responsivity 62 of the blue color sensor 18 and the spectral responsivity 58 of the green color sensor 16 overlap. For light having wavelengths that fall with the co-sensing wavelength band 64, both the blue sensor 18 and the green sensor 16 will yield a signal. The spectral responsivity 60 of the red color sensor 17 is negligible in co-sensing wavelength band 64.

Moreover, in co-sensing wavelength band 64, the mean spectral responsivity 70 of the one type 16 of color sensor is different from the mean spectral responsivity 74 of the other type 18 of color sensor. The mean spectral responsivity 70 can be calculated by any procedure for averaging, such as the geometric, arithmetic and/or harmonic mean value or the median of the respective spectral responsivity 58, 60, 62 within the respective co-sensing wavelength band 64, 66, 68. Preferably, the mean spectral responsivities 70, 72, 74 of at least two types of color sensor, preferably of at least three types of color sensor, are different.

In co-sensing wavelength band 66, the spectral responsivities 58, 60, 62 overlap so that each color sensor 8 will yield a signal if illuminated with wavelengths that fall within the co-sensing wavelength band 66. Again, reference numerals 70, 72, 74 denote the mean spectral responsivities. In co-sensing wavelength band 68, the relative mean spectral responsivities 70, 72 and 74 have shifted compared to co-sensing wavelength band 66. From the top of FIG. 5, it is therefore clear that, by changing the location and/or width—as e.g. determined by the center frequency or at least one cut-off frequency—of a co-sensing wavelength band, the mean spectral responsivities 70, 72, 74 may be adjusted. This dependency may be used to maximize the dynamic range of a digital monochrome HDR output image 38 computed from the digital monochrome input images 6 if the color bands recorded by the different types of sensor are restricted to a co-sensing wavelength band.

For example, the co-sensing wavelength band may be selected such that the mean spectral responsivities 70, 72, 74 are, at least approximately, equidistantly spaced in a linear or log scale. Hereby, variations of +/−20% of the difference between subsequent mean spectral responsivities 70, 72, 74 still count as equidistant.

In another approach, which can be used alternatively or cumulatively, a co-sensing wavelength band is selected where there is at least one mean spectral responsivity 70, 72, 74 at approximately half the normalized spectral responsivity $R_{0.5}$. Again, a variation of +/−20% relative to $R_{0.5}$ is still considered to correspond to $R_{0.5}$.

Further, again alternatively or cumulatively, the co-sensing wavelength band may be shifted so that the differences between the mean spectral responsivities 70, 72, 74 are maximized in the chosen co-sensing wavelength band. Such a maximization of the differences may be performed by maximizing the sum, product or any other norm of the differences between the mean spectral responsivities.

As used in this application, the spectral responsivity of a type of color sensor is representative of its response to incident light at a specific wavelength $\lambda$. The spectral responsivity may specifically relate to the ratio of the electrical output per optical input, i.e. not only include the optical wavelength-dependent properties of the type of color sensor, but also its electrical and electronic properties. At the very least, however, the spectral responsivity relates to the optical properties of the respective type of color sensor.

For creating and/or adjusting the co-sensing wavelength band 64, 66, 68, the band-pass filter 32 (FIG. 1) is preferably used. The pass band 34 defines the co-sensing wavelength band in which the different types of color sensor record the digital monochrome input images 6.

For example, a co-sensing wavelength band 64, 66, 68, or any other co-sensing wavelength band not shown in FIG. 5, may be selected by exchanging the band-pass filter 32 manually and thus filtering the light incident on the color sensor 8 with a different pass band 34. In the middle section of FIG. 5, three different pass bands 34 are shown which may be selected by using different band-pass filters 32. Preferably, only one pass band 34 is used at any one time. Of course, any other pass band 34 may be selected, as long as it overlaps, i.e. coincides, with a wavelength band in which there are at least two non-negligible or non-zero spectral responsivities 58, 60 and/or 62, i.e. results in a co-sensing wavelength band.

It is, however, preferred that the band-pass filter 32 is a tunable band-pass filter 32. This means that at least one of the following filter characteristics 77 may be modified: the upper cut-off frequency or, equivalently, the lower cut-off wavelength $\lambda_l$; the upper cut-off frequency or lower cut-off wavelength $\lambda_u$; the center frequency or center wavelength $\lambda_c$; the bandwidth 75 (FIG. 4) the Q-factor, i.e. the center frequency divided by the bandwidth 75, and/or the filter roll-off 76, i.e. the attenuation at the cut-off wavelengths $\lambda_l$, $\lambda_u$; or any other filter characteristic 77 in addition to the above.

Using a tunable band-pass filter 32 allows the pass band 34 to be quickly adjusted in order to select a co-sensing wavelength band 64, 66, 68 which yields the best results, in particular maximum contrast, for the digital monochrome HDR output image 38 (FIG. 1).

Moreover, if a tunable band-pass filter 32 is used, an automatic adjustment, in particular a feedback control, of any of the filter characteristics 77 may be implemented using e.g. a filter controller 78 (FIG. 1), which may be part of the HDR image generator 40 or be a separate electronic component such as a CPU or an ASIC and/or be a software component.

As an example of such a feedback control, the HDR image generator 40 may be configured to compute the dynamic range within each of the digital monochrome input images 6 and/or of the digital monochrome HDR output image 38 and adjust at least one of the filter characteristics 77 to maximize this dynamic range. For this, the HDR image generator 40 may comprise a memory section 80 (FIG. 1) in which a look-up table representative of the spectral responsivity curves 58, 60, 62, as shown e.g. in the topmost part of FIG. 5, is stored. By looking up the spectral responsivities of the different types of color sensor at a pass band 34, the filter controller 78 may compute, e.g. for a fixed filter bandwidth 74, a position of a co-sensing wavelength band within the tunable range of the band-pass filter 32 that maximizes contrast in the digital monochrome HDR output image 38 and/or any of the digital monochrome input images 6 for a given input image 4, 6. Other criteria according to which an automatic adaptation of the pass band 34 may be carried out have been explained above, such as maximizing the difference between the mean spectral responsivities.

In the bottom part of FIG. 5, the fluorescence spectra 82, 84 of two different fluorophores 22 are shown schematically. It can be seen that, for example in co-sensing wavelength band 68, the fluorescence intensity F of both fluorophores 22 will be low. For the fluorophore having fluorescence spectrum 84, it is best to use the co-sensing wavelength band 70 because it coincides with the wavelength $\lambda_F$ where the fluorescence emission is at its maximum. This will lead to a very high contrast in the digital monochrome HDR output image 38.

In the case of the fluorophore having fluorescence spectrum 82, both the co-sensing wavelength bands 64 and 66 may lead to good results. However, although co-sensing wavelength band 64 includes $\lambda_F$ from fluorescence spectrum 82, the signal of only two color sensors may be used, as the mean responsivity 60 of the red color sensor 16 is zero or negligible in this co-sensing wavelength band 64. Therefore, depending on the image characteristics of the digital monochrome input images 6 and/or the digital monochrome HDR output image 38, shifting the pass band 34 to a co-sensing wavelength band 66 may be preferable.

This demonstrates that the fluorophore may also be selected depending on the spectral responsivities of the different types of color sensor to achieve optimum results. In particular, the fluorophore should have a strong fluorescence in the available co-sensing wavelength bands and, at the same time, that the different types of color sensor should have sufficiently different spectral responsivities.

Figure 6:
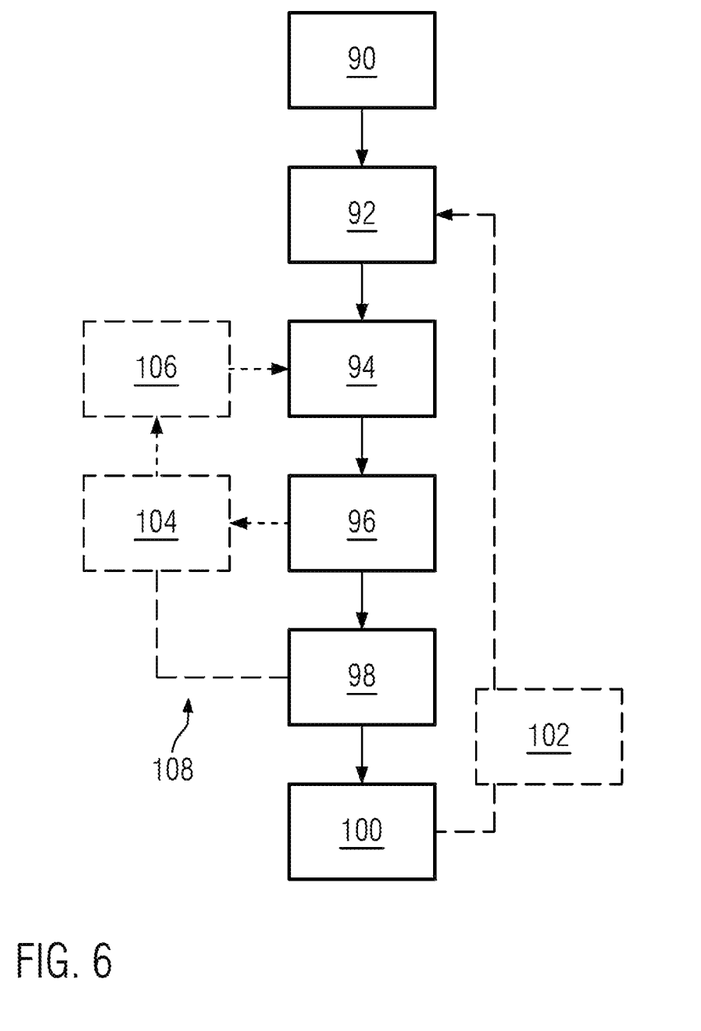
FIG. 6 shows a schematic representation of a flowchart for the method according to the invention.

FIG. 6 provides an overview of the process for obtaining a digital monochrome HDR output image 38 using the digital monochrome input images 6 of the fluorescence in the object 30.

In optional step 90, a fluorophore 22 is selected, of which the fluorescence spectrum 82, 84 overlaps with a co-sensing wavelength band. This step ensures that there will be sufficient fluorescence intensity generated in a wavelength band, in which at least two color sensors 8 will produce a sufficiently large output signal.

Further, in step 90, a band-pass filter 32 may be selected, of which the pass band 34 defines a co-sensing wavelength band which is preferably narrower than the fluorescence spectrum of the fluorophore.

In the next step 92, the fluorescence excitation light is provided to trigger the fluorescence in the fluorophore 22.

Next, in step 94, the fluorescence emitted by the fluorophore, preferably along with any reflected light, is filtered by the band-pass filter 32 in order to restrict it to the co-sensing wavelength band.

In step 96, digital monochrome input images 6 are acquired, preferably for at least two, most preferably for each color channel of color camera 2. The digital monochrome input images 6 are preferably acquired at the same time, i.e. as part of the same frame 21 or the same digital color input image 4. The images 4, 6 may be stereoscopic.

In step 98, the digital monochrome HDR output image 38 is computed from the digital monochrome input images 6. The digital monochrome HDR output image 38 may be three-dimensional or stereoscopic.

In step 100, the digital monochrome HDR output image 38 is displayed on at least one display device 48.

If the digital monochrome HDR output image 38 does not exhibit satisfactory contrast, a new band-pass filter 32, a new pass band 34 and/or a new fluorophore 22 may be chosen in step 102. If a tunable band-pass filter 32 is used, computation of a new pass band 34 may be manually triggered at this stage. Step 102 may be carried out at any time once a digital monochrome HDR image 38 is displayed.

In step 104, an image parameter, such as the dynamic range in at least one of the digital monochrome input images 6 and/or of the digital monochrome HDR output image 38 may be computed. In addition or alternatively, the location of the mean spectral responsivities in the current co-sensing wavelength band may be determined. From this, and by e.g. using a look-up table representing the spectral responsivities of the different types of color sensor used in the camera, a pass band 34 having filter characteristics 77 that maximize the contrast in the digital monochrome HDR output image 38 is computed. The required filter characteristics 77 may be displayed for a user to manually select a band-pass filter 32 or manually adjust a tunable band-pass filter 32. The filter characteristics may also be communicated electronically and automatically for the filter controller 78 to adjust the pass band 34.

In step 106, the band-pass filter 32 is automatically adjusted or exchanged manually to exhibit to the new filter characteristics 77. Steps 104 and 106 establish a feedback control 108 for automatically adjusting the optimum pass band 34.

The above steps can be performed in real-time so that the computation of the digital monochrome HDR output image 38 can be performed at the frame rate of a video sequence or stream.

REFERENCE NUMERALS 1 image acquisition system
2 color camera
3 medical observation apparatus
4 digital color input image
6 digital monochrome input image
8 color sensor
10 input pixel
12 mosaic filter arrangement
13 green filter
14 red filter
15 blue filter
16 green sensor
17 red sensor
18 blue sensor
20 surface
21 frame
22 fluorophore
24 live tissue
26 light source
28 light from light source
30 object
32 band-pass filter
34 pass band
36 optical path
37 optical acquisition system
38 digital monochrome HDR output image
40 HDR image generator
41 hardware device
42 general-purpose computer
44 input interface
46 output interface
48 display device
50 eyepiece
52 AR goggles
54 monitor
56 output pixel
58 spectral responsivity of different color sensor
60 spectral responsivity of different color sensor
62 spectral responsivity of different color sensor
64 co-sensing wavelength band
66 co-sensing wavelength band
68 co-sensing wavelength band
70 mean spectral responsivity
72 mean spectral responsivity
74 mean spectral responsivity
75 bandwidth
76 roll-off
77 filter characteristics
78 filter controller
80 memory section
82 fluorescence spectrum
84 fluorescence spectrum
90 process step
92 process step
94 process step
96 process step
98 process step
100 process step
102 process step
104 process step
106 process step
108 feedback control loop
R spectral responsivity
T transmittivity
F fluorescence intensity
$\lambda$ wavelength
$\lambda_c$ wavelength at center frequency
$\lambda_l$ wavelength at lower cut-off frequency
$\lambda_u$ wavelength at upper cut-off frequency
$\lambda^F$ wavelength at maximum fluorescence

What is claimed is:

1. An image acquisition system (1) for a microscope or an endoscope, for processing digital input images (4, 6) of a fluorophore (22) having a fluorescence spectrum (82, 84), the image acquisition system (1) comprising:
   a color camera (2),
   the color camera (2) having at least two different types (16, 17, 18) of color sensor (8) at a plurality of input pixels (10), each type (16, 17, 18) of color sensor (8) generating a different digital monochrome input image (6) comprising the input pixels (10) and having a different spectral responsivity (58, 60, 62),
   the color camera (2) further comprising at least one co-sensing wavelength band (64, 66, 68) in which the spectral responsivities of at least two types of color sensor overlap, wherein the co-sensing wavelength band (64, 66, 68) overlaps with the fluorescence spectrum (82, 84) of the fluorophore (22);
   an HDR image generator (40) coupled to the color camera (2);
   wherein the HDR image generator (40) is configured to compute a digital monochrome HDR output image (38) from the at least two digital monochrome input images (6);
   an optical band-pass filter (32) located in front of the color camera (2), the optical band-pass filter (32) having a pass band (34), the pass band (34) defining the co-sensing wavelength band (64, 66, 68); and a memory section (80) comprising a representation of the spectral responsivities (58, 60, 62) of the different types (14, 16, 18) of color sensor (8) of the color camera (2), and wherein the image acquisition system (1) is configured to automatically adjust the pass band (34) depending on the spectral responsivities (58, 60, 62).

2. The image acquisition system (1) according to claim 1, wherein the pass band (34) of the band-pass filter (32) overlaps with the fluorescence spectrum (82, 84) of the fluorophore (22).

3. The image acquisition system (1) according to claim 1, the band-pass filter (32) comprising a tunable pass band (34), the pass band (34) being tunable with respect to at least one filter characteristic (77), the at least one filter characteristic (77) comprising at least one of: a center frequency, at least one cut-off frequency, a roll-off (76), a bandwidth (75), and a Q-factor.

4. An image acquisition system (1) for a microscope or an endoscope, for processing digital input images (4, 6) of a fluorophore (22) having a fluorescence spectrum (82, 84), the image acquisition system (1) comprising:
   a color camera (2),
   the color camera (2) having at least two different types (16, 17, 18) of color sensor (8) at a plurality of input pixels (10), each type (16, 17, 18) of color sensor (8) generating a different digital monochrome input image (6) comprising the input pixels (10) and having a different spectral responsivity (58, 60, 62),
   the color camera (2) further comprising at least one co-sensing wavelength band (64, 66, 68) in which the spectral responsivities of at least two types of color sensor overlap, wherein the co-sensing wavelength band (64, 66, 68) overlaps with the fluorescence spectrum (82, 84) of the fluorophore (22);
   an HDR image generator (40) coupled to the color camera (2);
   wherein the HDR image generator (40) is configured to compute a digital monochrome HDR output image (38) from the at least two digital monochrome input images (6);
   an optical band-pass filter (32) located in front of the color camera (2), the optical band-pass filter (32) having a pass band (34), the pass band (34) defining the co-sensing wavelength band (64, 66, 68);
   the band-pass filter (32) comprising a tunable pass band (34), the pass band (34) being tunable with respect to at least one filter characteristic (77), the at least one filter characteristic (77) comprising at least one of: a center frequency, at least one cut-off frequency, a roll-off (76), a bandwidth (75), and a Q-factor; and
   a filter controller (78) coupled to the HDR image generator (40) for modifying the pass band (34) of the band-pass filter (32) depending on image characteristics of the digital monochrome input images (6) and/or the digital monochrome HDR output image (38).

5. An image acquisition system (1) for a microscope or an endoscope, for processing digital input images (4, 6) of a fluorophore (22) having a fluorescence spectrum (82, 84), the image acquisition system (1) comprising:
   a color camera (2),
   the color camera (2) having at least two different types (16, 17, 18) of color sensor (8) at a plurality of input pixels (10), each type (16, 17, 18) of color sensor (8) generating a different digital monochrome input image (6) comprising the input pixels (10) and having a different spectral responsivity (58, 60, 62),
   the color camera (2) further comprising at least one co-sensing wavelength band (64, 66, 68) in which the spectral responsivities of at least two types of color sensor overlap, wherein the co-sensing wavelength band (64, 66, 68) overlaps with the fluorescence spectrum (82, 84) of the fluorophore (22);
   an HDR image generator (40) coupled to the color camera (2);
   wherein the HDR image generator (40) is configured to compute a digital monochrome HDR output image (38) from the at least two digital monochrome input images (6);
   an optical band-pass filter (32) located in front of the color camera (2), the optical band-pass filter (32) having a pass band (34), the pass band (34) defining the co-sensing wavelength band (64, 66, 68);
   the band-pass filter (32) comprising a tunable pass band (34), the pass band (34) being tunable with respect to at least one filter characteristic (77), the at least one filter characteristic (77) comprising at least one of: a center frequency, at least one cut-off frequency, a roll-off (76), a bandwidth (75), and a Q-factor; and
   a control loop (108) for automatically modifying the pass band (34) depending on an image characteristic of at least one of the digital monochrome input images (6) and/or the digital monochrome HDR output image (38).

6. A medical observation apparatus (3) comprising:
   an image acquisition system (1) for processing digital input images (4, 6) of a fluorophore (22) having a fluorescence spectrum (82, 84), the image acquisition system (1) comprising:
   a color camera (2),
   the color camera (2) having at least two different types (16, 17, 18) of color sensor (8) at a plurality of input pixels (10), each type (16, 17, 18) of color sensor (8) generating a different digital monochrome input image (6) comprising the input pixels (10) and having a different spectral responsivity (58, 60, 62),
   the color camera (2) further comprising at least one co-sensing wavelength band (64, 66, 68) in which the spectral responsivities of at least two types of color sensor overlap, wherein the co-sensing wavelength band (64, 66, 68) overlaps with the fluorescence spectrum (82, 84) of the fluorophore (22);
   an HDR image generator (40) coupled to the color camera (2);
   wherein the HDR image generator (40) is configured to compute a digital monochrome HDR output image (38) from the at least two digital monochrome input images (6);
   an optical band-pass filter (32) located in front of the color camera (2), the optical band-pass filter (32) having a pass band (34), the pass band (34) defining the co-sensing wavelength band (64, 66, 68); and
   a memory section (80) comprising a representation of the spectral responsivities (58, 60, 62) of the different types (14, 16, 18) of color sensor (8) of the color camera (2), and wherein the image acquisition system (1) is configured to automatically adjust the pass band (34) depending on the spectral responsivities (58, 60, 62);
   wherein the medical observation apparatus (3) is a microscope or an endoscope.

7. A method for creating a digital monochrome HDR output image (38) of a fluorescing fluorophore (22) from at least two digital monochrome input images (6) each having a plurality of input pixels (10), the method comprising the steps of:

acquiring the at least two digital monochrome input images (6) of the fluorescing fluorophore (22) using at least two different types (16, 17, 18) of color sensor (8), the at least two different types of color sensor having a different spectral responsivity (58, 60, 62) and comprising at least one co-sensing wavelength band (64, 66, 68) in which the spectral responsivities of at least two types of color sensor overlap;

selecting the fluorescing fluorophore (22) to have a fluorescence spectrum (82, 84) which overlaps with the co-sensing wavelength band; and computing a digital monochrome HDR output image (38) from the at least two digital monochrome input images (6).

8. The method according to claim 7, further comprising the step of filtering the fluorescent light from the fluorophore (22) directed to the color sensors (8) using an optical band-pass filter (32) having a pass band (34) which overlaps with the co-sensing wavelength band (64, 66, 68).

9. The method according to claim 7, further comprising the step of modifying the pass band (34) to increase contrast in the digital monochrome HDR output image (38).

10. The method according to claim 9, further comprising the step of automatically modifying the pass band (34) depending on an image characteristic of at least one of the digital monochrome input images (6) and/or the digital monochrome HDR output image (38).

11. The method according to claim 9, further comprising the step of modifying the pass band (34) depending on a difference between the spectral responsivities (58, 60, 62) of the at least two different types (16, 17, 18) of color sensor (8) within the pass band (34).

12. The method according to claim 9, further comprising the step of recording the at least two digital monochrome input images (6) using the at least two different types (16, 17, 18) of color sensor (8).

13. A non-transitory computer-readable medium storing a program causing a computer to execute the method according to claim 7.

* * * * *